United States Patent
Van Der Heide et al.

(10) Patent No.: US 10,450,249 B2
(45) Date of Patent: Oct. 22, 2019

(54) PROCESS FOR THE PRODUCTION OF GLYCOLS

(71) Applicant: SHELL OIL COMPANY, Houston, TX (US)

(72) Inventors: Evert Van Der Heide, Amsterdam (NL); Pieter Huizenga, Amsterdam (NL); Dionysius Jacobus Maria De Vlieger, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/322,568

(22) PCT Filed: Aug. 2, 2017

(86) PCT No.: PCT/EP2017/069568
§ 371 (c)(1),
(2) Date: Feb. 1, 2019

(87) PCT Pub. No.: WO2018/024787
PCT Pub. Date: Feb. 8, 2018

(65) Prior Publication Data
US 2019/0202760 A1    Jul. 4, 2019

(30) Foreign Application Priority Data

Aug. 4, 2016 (EP) .................... 16182811

(51) Int. Cl.
| | |
|---|---|
| *C07C 29/00* | (2006.01) |
| *C07C 31/00* | (2006.01) |
| *B01J 23/00* | (2006.01) |
| *C07C 29/132* | (2006.01) |
| *C07C 29/76* | (2006.01) |
| *B01J 23/04* | (2006.01) |
| *B01J 23/30* | (2006.01) |
| *C07C 31/20* | (2006.01) |

(52) U.S. Cl.
CPC ............ *C07C 29/132* (2013.01); *B01J 23/04* (2013.01); *B01J 23/30* (2013.01); *C07C 29/76* (2013.01); *C07C 31/202* (2013.01); *C07C 31/205* (2013.01)

(58) Field of Classification Search
CPC ..... C07C 29/132; C07C 29/76; C07C 31/202; C07C 31/205; B01J 23/04; B01L 23/30
See application file for complete search history.

(56) References Cited

U.S. PATENT DOCUMENTS

| | | |
|---|---|---|
| 2011/0046419 A1 | 2/2011 | Zhang et al. |
| 2011/0312487 A1 | 12/2011 | Chen et al. |
| 2011/0313212 A1 | 12/2011 | Kalnes et al. |
| 2018/0244594 A1 | 8/2018 | Colijn et al. |
| 2018/0326405 A1 | 11/2018 | Edulji et al. |

FOREIGN PATENT DOCUMENTS

| | | |
|---|---|---|
| CN | 102675045 A | 9/2012 |
| CN | 103731258 A | 4/2014 |
| CN | 102643165 B | 7/2014 |
| WO | 2013015955 A2 | 1/2013 |
| WO | 2016114660 A1 | 7/2016 |
| WO | 2016114661 A1 | 7/2016 |

OTHER PUBLICATIONS

International Search Report and Written Opinion received for PCT Patent Application No. PCT/EP2017/069568, dated Oct. 5, 2017, 8 pages.
Ji et al., "Direct Catalytic Conversion of Cellulose into Ethylene Glycol Using Nickel-Promoted Tungsten Carbide Catalysts", Angewandte Chemie International Edition, vol. 47, Issue No. 44, Oct. 20, 2008, pp. 8510-8513.
Zhang et al., "Kinetic Study of Retro-Aldol Condensation of Glucose to Glycolaldehyde With Ammonium Metatungstate as the Catalyst", AIChE Journal, Nov. 2014, vol. 60, Issue No. 11, pp. 3804-3813.
Liu et al., "Tungsten Trioxide Promoted Selective Conversion of Cellulose Into Propylene Glycol and Ethylene Glycol on a Ruthenium Catalyst", Angewandte Chemie International Edition, vol. 51, Issue No. 13, Feb. 24, 2012, pp. 3249-3253.

*Primary Examiner* — Sikarl A Witherspoon

(57) ABSTRACT

The invention provides a process for the preparation of glycols from a saccharide-containing feedstock in a reactor system, said process comprising: i) providing a first feed stream comprising said saccharide-containing feedstock in a first solvent at a N temperature of no more than 160° C.; ii) providing a second feed stream comprising a tungsten-based retro-aldol catalytic species and an alkali metal containing species in a second solvent at a temperature in the range of from 150 to 250° C.; iii) combining the first feed stream and the second feed stream, before they are provided to the reactor system, to form a combined feed stream; iv) providing the combined feed stream to the reactor system and operating the reactor at a temperature in the range of from 150° C. to 250° C.; and v) also contacting the combined feed stream with a hydrogenation catalytic species in the presence of hydrogen, wherein the molar ratio of alkali metal:tungsten in the combined feed stream is in the range of from 0.55 to 6.

10 Claims, 2 Drawing Sheets

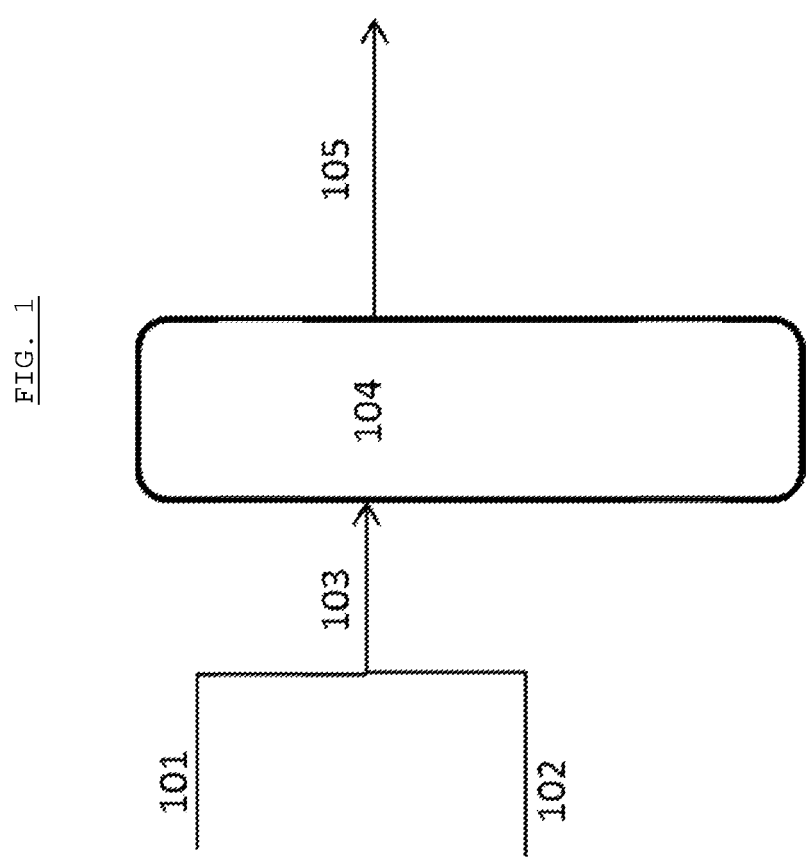

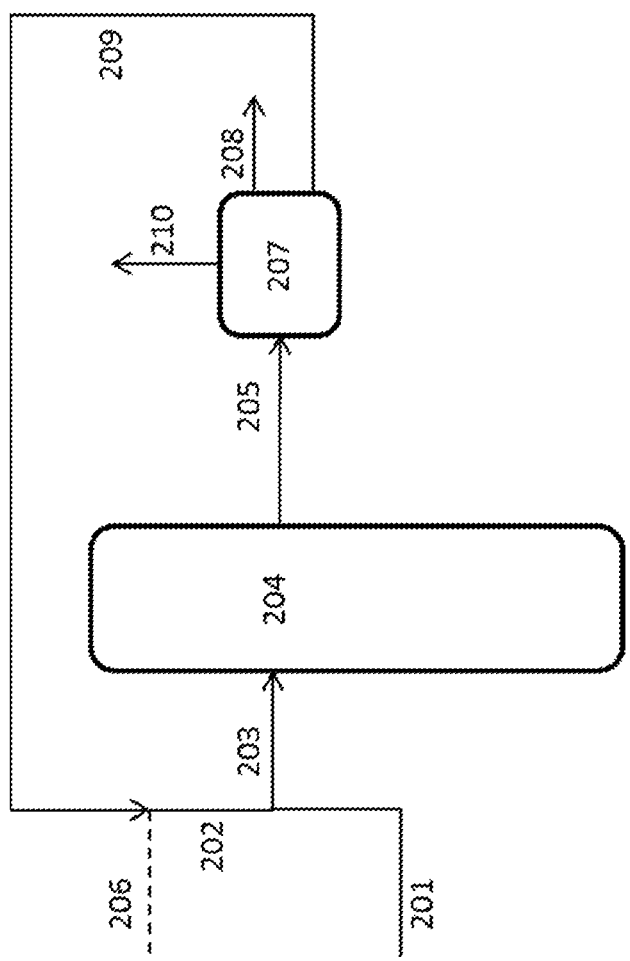

US 10,450,249 B2

PROCESS FOR THE PRODUCTION OF GLYCOLS

CROSS REFERENCE TO RELATED APPLICATIONS

This is a national stage application of International Application No. PCT/EP2017/069568, filed 2 Aug. 2017, which claims benefit of priority to European Patent Application No. 16182811.6, filed 4 Aug. 2016.

FIELD OF THE INVENTION

The present invention relates to a process for the production of glycols, in particular monoethylene glycol and monopropylene glycol, from a saccharide-containing feedstock.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers such as polyethylene terephthalate (PET).

Said glycols are currently made on an industrial scale by hydrolysis of the corresponding alkylene oxides, which are the oxidation products of ethylene and propylene, generally produced from fossil fuels.

In recent years increased efforts have been focussed on reducing the reliance on fossil sources as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. Current methods for the conversion of saccharides to glycols revolve around a hydrogenation/hydrogenolysis process as described in Angew. Chem. Int. Ed. 2008, 47, 8510-8513. Development of this technology has been on-going.

A preferred methodology for a commercial scale process would be to use continuous flow technology, wherein feed is continuously provided to a reactor and product is continuously removed therefrom. By maintaining the flow of feed and the removal of product at the same levels, the reactor content remains at a more or less constant volume. Continuous flow processes for the production of glycols from saccharide feedstock have been described in US20110313212, CN102675045, CN102643165, WO2013015955 and CN103731258.

Reported processes for the conversion of saccharides to glycols generally require two catalytic species in order to perform the hydrogenation/hydrogenolysis process. The first catalytic species catalyses the hydrogenolysis reaction, which is postulated to have a retro-aldol mechanism, and the second catalytic species is present for the hydrogenation reaction.

The catalytic species used for the hydrogenation reactions tend to be heterogeneous. However, the catalytic species suitable for the retro-aldol reactions are generally homogeneous in the reaction mixture.

The use of a homogeneous tungsten-containing species as the first 'retro-aldol' catalytic species has been reported widely, for example in US20110312487; US 201103046419; Angew. Chem. Int. Ed. 2012, 51, 3249-3253; AIChE Journal, 2014, 60 (11), pp. 3804-3813; and WO2016114661. The use of a sodium metatungstate-containing species as the retro-aldol catalytic species is disclosed in co-pending application EP 15195495.5.

The homogeneous tungsten-based catalysts typically used in a saccharides to glycols process may be susceptible to conversion to undesirable products, for example by reduction and precipitation of the metal (tungsten). Precipitated solids in a reactor system can lead to blocked lines and clogging as well as undesirable chemical and/or physical reactions of the tungsten metal with other species present (e.g. catalyst poisoning).

It is clearly desirable to maximise the yields of MEG and MPG in saccharides to glycols processes and to deliver a process that can be carried out in a commercially viable manner. The market for MEG is generally more valuable than that for MPG, so a process particularly selective toward MEG would be advantageous.

Saccharide-containing feed streams are subject to degradation when held at the elevated temperatures required for their conversion to glycols for any significant period of time. Saccharide degradation includes conversion to less useful saccharides (e.g. glucose conversion to fructose) as well as other undesirable non-saccharide by-products. Degradation and/or conversion may also occur at lower temperatures which are experienced during the heating up (including mixing) of the feedstock to the reaction temperature. Saccharide degradation is undesired, as product yields are lower and fouling might occur, in addition to separation of desired product from degraded products and waste handling, including waste water treatment. Saccharide degradation has typically been reduced by limiting the residence time of the saccharide-containing feed at elevated temperatures before the feed is introduced into the reactor and equalizes in temperature and concentration with the reactor liquid content, i.e. during the time present in feed lines and in the reactor before mixing is complete and reaction occurs. Limitation of saccharide degradation to 5% or less is difficult, as reaction times for such degradation at temperatures higher than about 160° C. are in the order of a few seconds. Liquid handling within such time frames are difficult in industrial practice and, therefore, highly undesirable.

One undesirable side-reaction of saccharides at high temperature, in the conversion of saccharides to glycols, involves the conversion of glucose to fructose. It is postulated that when fructose undergoes hydrogenolysis in a retro-aldol process, C3 fragments are produced, increasing the relative amount of MPG formed compared with MEG.

The use of a buffer in a process for the conversion of saccharides to glycols has been described in co-pending application EP15184082.4. Such buffers are used to maintain the pH in the reactor within a preferred range and are typically alkali metal, preferably sodium, containing salts.

It is desirable to provide an improved process for the conversion of saccharides to glycols in which the yield of glycols and, preferably, the yield of MEG is maximised.

SUMMARY OF THE INVENTION

The present invention, therefore, provides a process for the preparation of glycols from a saccharide-containing feedstock in a reactor system, said process comprising:
i) providing a first feed stream comprising said saccharide-containing feedstock in a first solvent at a temperature of no more than 160° C.;
ii) providing a second feed stream comprising a tungsten-based retro-aldol catalytic species and an alkali metal containing species in a second solvent at a temperature in the range of from 150 to 250° C.;

iii) combining the first feed stream and the second feed stream, before they are provided to the reactor system, to form a combined feed stream;

iv) providing the combined feed stream to the reactor system and operating the reactor at a temperature in the range of from 150° C. to 250° C.; and v) also contacting the combined feed stream with a hydrogenation catalytic species in the presence of hydrogen, wherein the molar ratio of alkali metal:tungsten in the combined feed stream is in the range of from 0.55 to 6.

BRIEF DESCRIPTION OF THE DRAWINGS

FIGS. 1 and 2 are schematic diagrams of exemplary, but non-limiting, embodiments of the process of the present invention.

DETAILED DESCRIPTION OF THE INVENTION

The present inventors have surprisingly found that, by maintaining a saccharide-containing feed stream at a temperature of no more than 160° C. before it is combined with a second feed stream comprising a tungsten-based retro-aldol catalytic species and an alkali metal, the products formed from saccharide degradation that cannot be converted to MEG in the same efficiency as glucose (theoretical carbon selectivity of 100% to MEG), is reduced in a process for the production of glycols from a saccharide-containing feedstock. The molar ratio of alkali metal:tungsten in the combined feed stream is maintained in the range of from 0.55 to 6. It has been found that, under these conditions, although saccharide degradation/conversion still occurs, a high selectivity towards the formation of products that may still be converted to MEG in the same efficiency as glucose (theoretical carbon selectivity of 100% to MEG), is obtained. Increased yields of desirable glycols, in particular MEG, can be achieved, enabling commercially applicable residence times.

The saccharide-containing feedstock preferably comprises or is derived from at least one saccharide selected from the group consisting of monosaccharides, disaccharides, oligosaccharides and polysaccharides.

Saccharides, also referred to as sugars or carbohydrates, comprise monomeric, dimeric, oligomeric and polymeric aldoses, ketoses, or combinations of aldoses and ketoses, the monomeric form comprising at least one alcohol and a carbonyl function, being described by the general formula of $C_nH_{2n}O_n$ (n=4, 5 or 6). Typical $C_4$ monosaccharides comprise erythrose and threose, typical $C_5$ saccharide monomers include xylose and arabinose and typical $C_6$ sugars comprise aldoses like glucose, mannose and galactose, while a common $C_6$ ketose is fructose. Examples of dimeric saccharides, comprising similar or different monomeric saccharides, include sucrose, maltose and cellobiose. Saccharide oligomers are present in corn syrup. Polymeric saccharides include cellulose, starch, glycogen, hemicellulose, chitin, and mixtures thereof.

If the saccharide-containing feedstock used comprises or is derived from oligosaccharides or polysaccharides, it is preferable that it is subjected to pre-treatment before being used in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment. However, after said pre-treatment, the starting material still comprises mainly monomeric and/or oligomeric saccharides. Said saccharides are, preferably, soluble in the reaction solvent.

Preferably, the saccharide-containing feedstock, after any pre-treatment, comprises saccharides selected from glucose, starch and/or hydrolysed starch. Hydrolysed starch comprises glucose, sucrose, maltose and oligomeric forms of glucose. Said saccharide is suitably present as a solution, a suspension or a slurry in the first solvent.

The first solvent may be water or a $C_1$ to $C_6$ alcohol or polyalcohol (including sugar alcohols), ethers, and other suitable organic compounds or mixtures thereof. Preferred $C_1$ to $C_6$ alcohols include methanol, ethanol, 1-propanol and iso-propanol. Polyalcohols of use include glycols, particularly products of the hydrogenation/retro-aldol reaction, glycerol, erythritol, threitol, sorbitol and mixtures thereof. Preferably, the solvent comprises water.

The temperature of the first feed stream is maintained at a temperature no more than 160° C. before it is combined with the second feed stream.

Preferably, the temperature of the first feed stream is maintained such that no more than 5 wt %, more preferably no more than 1 wt %, even more preferably no more than 0.5 wt % of the saccharide contained therein undergoes any conversion, prior to the first feed stream being combined with the second feed stream. Such conversion/degradation may be controlled using a combination of factors such as temperature and residence time.

The second feed stream comprises a tungsten-based retro-aldol catalytic species and an alkali metal containing species in a second solvent.

Suitable tungsten-based retro-aldol catalytic species preferably comprises one or more material selected from the list consisting of tungstic acid, ammonium tungstate, ammonium metatungstate, ammonium paratungstate, silver tungstate, zinc tungstate, zirconium tungstate, tungstate compounds comprising at least one Group 1 or 2 element, metatungstate compounds comprising at least one Group 1 or 2 element, paratungstate compounds comprising at least one Group 1 or 2 element, heteropoly compounds of tungsten including group 1 phosphotungstates, tungsten oxides and combinations thereof. Typically, the tungsten component is in a form other than a carbide, nitride, or phosphide.

The alkali metal in the alkali metal containing species is preferably lithium, sodium or potassium, more preferably sodium. Further, the alkali metal containing species is preferably present as or derived from a buffer, and/or any other component used to control or modify pH, and/or the tungsten-based retro-aldol catalytic species present in the reactor system.

The second feed stream is at a temperature in the range of from 150° C. to 250° C. Preferably, the temperature of the second feed stream is no more than 230° C. Preferably, the temperature of the second feed stream is at least 160° C. In one preferred embodiment the second feed stream is maintained at a temperature of no more than 10° C. below the temperature in the reactor system.

The second solvent is preferably selected from $C_1$ to $C_6$ alcohols or polyalcohols (including sugar alcohols), ethers, and other suitable organic compounds or mixtures thereof. Polyalcohols of use include glycols, particularly products of the hydrogenation/retro-aldol reaction, glycerol, erythritol, threitol, sorbitol and mixtures thereof.

The first feed stream and second feed streams are combined before being provided to the reactor system.

The weight ratio of the tungsten-based retro-aldol catalytic species (based on the amount of tungsten in said composition) to sugar in the combined feed stream is suitably in the range of from 1:1 to 1:1000.

The molar ratio of alkali metal:tungsten in the combined feed stream is maintained in the range of from 0.55 to 6.0. Preferably, the molar ratio of alkali metal:tungsten in the combined feed stream is maintained in the range of from 0.55 to 3.0, more preferably in the range of from 1.0 to 2.0.

If required, the combined feed stream may be pre-heated before being provided to the reactor system by any suitable means. Preferably, the combined feed stream is at a temperature of no more than 10° C. lower than the temperature in the reactor system before being provided to the reactor system.

At the point where the combined feed stream is provided to the reactor system, preferably in the range of from 0.5 to 50 wt % of the saccharide, preferably glucose, may have undergone conversion. More preferably, no more than 20 wt % of the saccharide present has undergone conversion at this point.

The reactor system in which the process of the present invention is carried out may comprise one or more than one reactor and said reactor(s) may be of any suitable reactor type known in the art. In a preferred embodiment, the process of the present invention is carried out in a continuous manner and, thus, a suitable reactor system for a continuous reaction process, e.g. a continuous stirred tank reactor, is used.

The process for the preparation of glycols may be carried out in a 'one pot' process wherein both the retro-aldol and hydrogenation catalytic species are present simultaneously in a single reactor system. Alternatively, the retro-aldol step may be carried out in a first reactor or reaction zone and then the step of contacting the combined feed stream with a hydrogenation catalytic species in the presence of hydrogen is carried out in a second reactor or reaction zone. In this embodiment, the hydrogenation catalyst is only present in this second reactor or reactor zone. Further, in this embodiment wherein first and second reaction zones or reactors are present, said reaction zones or reactors are physically distinct from one another. Each reaction zone may be an individual reactor or reactor vessel or the zones may be contained within one reactor vessel.

The temperature in the reactor system is in the range of from 150° C. to 250° C. Preferably, the temperature in the reactor system is no more than 230° C. Preferably, the temperature in the reactor system is at least 160° C.

The pH in the reactor system is preferably at least 2.0, more preferably at least 2.5. The pH in the reactor system is preferably at most 8.0, more preferably at most 6.0. Preferably, the pH is maintained by using a buffer. Examples of suitable buffers include, but are not limited to, acetate buffers, phosphate buffers, lactate buffers, glycolate buffers, citrate buffers and buffers of other organic acids. In a preferred embodiment of the invention, the buffers are alkali metal, more preferably potassium, lithium or sodium, even more preferably sodium species.

After the process of the present invention, a product stream is removed from the reactor system. Preferably, when the process of the present invention is carried out continuously, said product stream is continuously removed from the reactor system.

At least a portion of the product stream is provided for separation and purification of the glycols contained therein. Steps for purification and separation may include solvent removal, catalyst separation, distillation and/or extraction in order to provide the desired glycol products. Any hydrogen present in the product stream may also be separated and, optionally, recycled.

Typically, said product stream is separated into at least a glycol product stream and a hydrocarbon heavies stream. The hydrocarbon heavies stream will contain sugar alcohols, other heavy organics, catalyst components (particularly homogeneous retro-aldol catalytic species) and buffer materials, if present. At least a portion of this stream may be recycled to the process.

In a preferred embodiment of the present invention, this hydrocarbon heavies stream will form at least a portion of the second feed stream. In this embodiment, the second solvent comprises the sugar alcohols and other heavy organics present in said hydrocarbon heavies stream.

The hydrogenation catalytic species is preferably heterogeneous and is retained or supported within a reactor. Further, said hydrogenation catalytic species also preferably comprises one or more materials selected from copper, tin and transition metals from groups 8, 9 or 10 or compounds thereof, with catalytic hydrogenation capabilities.

More preferably, the hydrogenation catalytic species comprises one or more metals selected from the list consisting of iron, cobalt, nickel, ruthenium, rhodium, palladium, iridium and platinum. This metal or metals may be present in elemental form or as compounds. It is also suitable that this component is present in chemical combination with one or more other ingredients in the hydrogenation catalytic species. It is required that the hydrogenation catalytic species has catalytic hydrogenation capabilities and it is capable of catalysing the hydrogenation of material present in the reactor.

In one embodiment, the hydrogenation catalytic species comprises metals supported on a solid support. In this embodiment, the solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Alternatively, the heterogeneous hydrogenation catalytic species may be present as Raney material, such as Raney nickel or Raney ruthenium, preferably present in a pelletised form.

The heterogeneous hydrogenation catalytic species is suitably preloaded into the reactor or reactor system before the reaction is started.

The hydrogenation step and, optionally, the retro-aldol step of the process of the present invention take place in the presence of hydrogen.

Hydrogen may be provided to part or all of the reactor system or to the first, second or combined feed stream. However, preferably hydrogen is provided to the reactor system and not to the first, second or combined feed stream.

Preferably, both steps take place in the absence of air or oxygen. In order to achieve this, it is preferable that the atmosphere under which the process takes place (e.g. in the reaction zones) be evacuated and replaced with first an inert gas, e.g. nitrogen or argon, and then, where required, hydrogen repeatedly, after loading of any initial contents, before the reaction starts.

DETAILED DESCRIPTION OF THE DRAWINGS

In these Figures, the first digit of each reference number refers to the Figure number (i.e. 1XX for FIG. 1 and 2XX for FIG. 2). The remaining digits refer to the individual features and the same features are provided with the same number in each Figure. Therefore, the same feature is numbered 104 in FIGS. 1 and 204 in FIG. 2.

In FIG. 1, a first feed stream 101, comprising a saccharide-containing feedstock in a first solvent and maintained at a temperature of no more than 160° C., is combined with a second feed stream 102 comprising a tungsten-based retro-aldol catalytic species and an alkali metal-containing species to form a combined feed stream 103. After optional preheating, the combined feed stream 103 is then provided to a reactor system 104. Within the reactor system 104, reaction in the presence of the tungsten-based retro-aldol catalytic species and contacting with a hydrogenation catalytic species in the presence of hydrogen and, preferably, a buffer species is carried out and a product stream 105 is removed from the reactor system.

FIG. 2 illustrates a preferred embodiment of the invention. In this embodiment, the product stream is subjected to one or more separation techniques 207 to provide a glycol product stream 208 and a hydrocarbon heavies stream 209. The hydrocarbon heavies stream will contain the tungsten-based retro aldol catalytic species as well as buffer species. At least a portion of the hydrocarbon heavies stream is used as at least a portion of the second feed stream 202. Optionally, fresh material 206 may be provided to the second feed stream. Hydrogen 210 separated one or more separation techniques 207 may optionally be recycled to the reactor system 204.

The present invention is further illustrated by the following Examples.

EXAMPLES

Examples 1 to 4 (Comparative)

Glucose to sorbitol hydrogenation was studied in continuous mode in a 100 ml Hastelloy autoclave (50 ml liquid hold-up). The reactor was connected to two separate feed lines for feeding solutions via HPLC pumps. The feed lines entered the reactor through a heated reactor lid, which is held at the reaction temperature. The saccharide feeds are therefore exposed to the reaction temperature before the feed contacts the reaction mixture, allowing for saccharide feedstock degradation. The total exposure time of the saccharide feedstock is defined as the time that the saccharide feedstock is subjected to elevated temperatures (>160° C.) before it contacts the reaction mixture. Exposure times of the saccharide solution in the feed section where varied by changing the inner diameter of the feed-tube from 1.76 mm to 250 μm.

The reactor was loaded with 3.5 g Raney Ni hydrogenation catalyst and pressurized to a total pressure of 120 bar. This pressure was a combination of water vapour pressure and $H_2$ that was fed at a rate of 3 NL/hr. An aqueous solution of 10 wt % glucose was fed to the reactor at a flowrate of 20 ml/hr through the first feed line with an inner diameter of either 1.76 mm or 250 μm. Water was fed via the second feed line at a rate of 20 ml/hr. The combined flow (40 ml/hr) resulted in a residence time in the reactor of 75 minutes and a glucose feed concentration of 5 wt %. Product yields were evaluated at different reaction temperatures. Products were analysed via HPLC.

Total organic carbon (TOC) analysis was conducted for Example 1 and confirmed that 95+% of the carbon fed was still present in the liquid product after the reaction, indicating that the missing carbon in the carbon balance can be attributed to a large extent to non-identified components in the reaction product, that were formed as a consequence of glucose degradation.

The retro-aldol catalytic species is not used in these Examples in order to simplify the product slate and to provide accurately comparable results. There Examples demonstrate the amount of glucose conversion/degradation that occurs at different residence times and temperatures. If 100% of glucose was present before hydrogenation can occur (i.e. 0% conversion/degradation), then 101% sorbitol should be the product. Lower amounts of sorbitol indicate higher amounts of glucose conversion/degradation.

Where a range of results is shown for any one temperature, a number of samples were taken at that temperature.

Table 1 shows a summary of sorbitol yields for Examples 1 to 4.

TABLE 1

| | Example No | | | |
|---|---|---|---|---|
| | 1 | 2 | 3 | 4 |
| | Exposure time* | | | |
| Temp (° C.) | 18.7 s | 18.7 s | 2.1 s | 2.1 s |
| | Sorbitol yield (wt %) | | | |
| 150 | 101.6 | — | — | — |
| 160 | 99.2 | — | — | — |
| 170 | 102.8 | — | — | — |
| 180 | 99 | — | — | — |
| 190 | 85.2 | — | — | — |
| 200 | 90 | 85.1-88.4 | 89.1-91.7 | 91.3-95.9 |
| 210 | 78.4 | — | — | — |
| 220 | 63.7 | 62.1 | 75.4 | 78.1-80.8 |
| 230 | 36.7 | — | — | 62.3-66.7 |

*Exposure time is defined as the time that the saccharide feedstock is subjected to elevated temperatures before it contacts the reaction mixture.

The glucose degradation is rather severe at 18.7 s exposure time. For example, at 230° C. and exposure time of 18.7 seconds, only ~60 wt % of the carbon fed is identified in the reaction product by HPLC analysis, and assuming that at least a portion of the sorbitol originates from the hydrogenation of un-degraded glucose, it can be seen that at least 60% of the glucose underwent degradation. The reduction of exposure time from 18.7 to 2.1 seconds (Examples 3 & 4) at the higher reaction temperatures showed a significant improvement in sorbitol yields.

Table 2 provides a more detailed product distribution for Example 4. These results show that even at this short exposure time, a lot of glucose conversion/degradation occurs at higher temperatures. Fructose exists in two isomers (alpha and beta) and both are present in a 50/50 ratio. One isomer is hydrogenated to sorbitol, while the other isomer is hydrogenated to mannitol. Formation of fructose can, therefore, be considered to be 2 times the mannitol yield. Table 2 shows that, at higher temperatures (e.g. 230° C.) a lot of mannitol was formed after hydrogenation, indicating that ~25% of the glucose degraded to fructose at a temperature of 230° C. and an exposure time of 2.1 s.

TABLE 2

| Product distribution of Example 4 (t = 2.1 s) | | | | | | |
|---|---|---|---|---|---|---|
| Temp | Yield (wt %) | | | | | |
| (° C.) | sorbitol | mannitol | erythritol | threitol | glycerol | MEG |
| 200 | 91.3 | 6.5 | 1.5 | 0.0 | 0.0 | 0.0 |
| 200 | 95.9 | 5.1 | 0.0 | 0.0 | 1.4 | 0.0 |
| 220 | 78.1 | 8.7 | 0.0 | 0.0 | 2.6 | 0.0 |

TABLE 2-continued

Product distribution of Example 4 (t = 2.1 s)

| Temp | Yield (wt %) | | | | | |
|---|---|---|---|---|---|---|
| (° C.) | sorbitol | mannitol | erythritol | threitol | glycerol | MEG |
| 200 | 80.8 | 9.1 | 1.1 | 0.7 | 2.8 | 0.6 |
| 230 | 62.3 | 13.0 | 1.9 | 1.5 | 4.2 | 1.2 |
| 230 | 65.5 | 12.6 | 1.8 | 1.4 | 4.5 | 1.1 |
| 230 | 64.8 | 12.5 | 1.8 | 1.4 | 4.2 | 1.2 |

Examples 5 to 8

A 3-D printed reactor was then used to study the effect of glucose degradation as a function of temperature (160-230° C.) and residence time; glucose only; in the presence of a buffer; in the presence of a tungsten-based retro-aldol catalytic species; and in the presence of a tungsten-based retro-aldol catalytic species and a buffer (Examples 5-8). This 3-D printed reactor has multiple channels with small internal diameter (<0.25 mm) that can be used to feed a solution through. The reactor is specifically designed so that it can rapidly heat up the solution that enters the reactor channels and also cool down the solution that exits the reactor.

Selectivity to desired or undesired products is defined as the % of converted glucose to desired or undesired products.

Desired products are defined as products that can still be converted in the hydrogenolysis reactor to MEG in the same efficiency as glucose (theoretical carbon selectivity of 100% to MEG), and include mannose, erythrose, threose, and glycolaldehyde.

Undesired products are defined as products that cannot be converted anymore in the hydrogenolysis reactor to MEG in the same efficiency as glucose (theoretical carbon selectivity of 100% to MEG), and include fructose, glyceraldehyde and MPG.

Some components have not been identified (mass balance <100%), and these are likely components that cannot be converted anymore in the hydrogenolysis reactor to MEG in the same efficiency as glucose (theoretical carbon selectivity of 100% to MEG), and are therefore considered un-desired products. These un-identified products haven't been taken into account in the selectivity calculations.

Example 5 (Comparative)

A solution of 1 wt % of glucose was fed to the reactor and the glucose conversion was studied at 5, 10 and 15 seconds residence time at temperatures of 160 to 230° C. Results are shown in Table 3. Fructose was a major component formed in these experiments. Formation of mannose was not observed in these experiments. Other identified products include erythrose, threose, glyceraldehyde, glycolaldehyde. It can be seen that glucose conversion/degradation in absence of tungsten species and buffer is highly unselectively towards desired products. A maximum selectivity of 18.6% to desired products is observed at 27% glucose conversion (Temp=230° C., t=15 s).

TABLE 3

| t (s) | T ° C. | Glucose conversion % | yield | | | Selectivity desired products % | Selectivity undesired products % |
|---|---|---|---|---|---|---|---|
| | | | fructose | mannose | Other* | | |
| 15 | 160 | 4.7 | 2.71 | — | 0.00 | 0.00 | 28.09 |
| 5 | 195 | 6.8 | 4.08 | — | 0.00 | 0.00 | 59.65 |
| 10 | 195 | 7.9 | 5.18 | — | 0.00 | 0.00 | 65.91 |
| 15 | 195 | 9.6 | 6.40 | — | 0.00 | 0.00 | 66.63 |
| 5 | 215 | 13.9 | 10.43 | — | 1.666 | 12.00 | 75.21 |
| 10 | 215 | 16.3 | 11.45 | — | 3.04 | 18.65 | 70.18 |
| 15 | 215 | 19.5 | 13.54 | — | 3.04 | 15.58 | 69.34 |
| 5 | 230 | 17.7 | 13.02 | — | 2.70 | 15.24 | 73.47 |
| 10 | 230 | 12.2 | 15.68 | — | 4.56 | 18.30 | 69.02 |
| 15 | 230 | 27.0 | 16.96 | — | 5.50 | 18.64 | 64.51 |

*other identified products

Example 6 (Comparative)

A solution of 1 wt % of glucose+buffer (3 g/L Acetic acid+6 g/L sodium acetate) was fed to the reactor and the glucose conversion was studied at 5, 10 and 15 seconds residence time at temperatures of 160 to 230° C.

Results are tabulated in Table 4. Fructose was a major component formed in these experiments. Formation of mannose was not observed in these experiments. Other identified products include erythrose, threose, glyceraldehyde, MPG and glycolaldehyde. It can be seen that glucose degradation in presence of buffer and absence of W-species is highly unselectively towards desired products. A maximum selectivity of only 22.0% to desired products is observed at 72% glucose conversion (Temp=230° C., t=15 s).

TABLE 4

| t (s) | T ° C. | Glucose conversion % | yield | | | Selectivity desired products % | Selectivity undesired products % |
|---|---|---|---|---|---|---|---|
| | | | fructose | mannose | Other* | | |
| 15 | 160 | 0.1 | 1.20 | — | 0.00 | 0.00 | — |
| 5 | 195 | 4.8 | 4.31 | — | 0.00 | 0.00 | 90.06 |
| 10 | 195 | 10.5 | 8.42 | — | 0.35 | 3.28 | 76.95 |
| 15 | 195 | 15.4 | 11.82 | — | 0.54 | 3.53 | 76.755 |
| 5 | 215 | 20.8 | 16.12 | — | 3.65 | 15.82 | 79.11 |
| 10 | 215 | 35.9 | 24.18 | — | 6.84 | 15.80 | 70.68 |
| 15 | 215 | 48.0 | 28.46 | — | 10.24 | 16.00 | 64.70 |
| 5 | 230 | 48.2 | 27.01 | — | 10.80 | 20.01 | 67.47 |
| 10 | 230 | 65.5 | 30.37 | — | 17.99 | 19.36 | 54.45 |
| 15 | 230 | 72.0 | 32.58 | — | 23.98 | 22.04 | 56.53 |

*other identified products

Example 7 (Comparative)

A solution of 1 wt % of glucose+2500 ppm W (in the form of sodium metatungstate) was fed to the reactor and the glucose conversion was studied at 5, 10 and 15 seconds residence time at temperatures of 195 to 230° C.

Results are tabulated in Table 5. Formation of fructose was not observed in these experiments. Mannose was a major component formed in these experiments. Other identified products include erythrose, threose, glyceraldehyde, MPG and glycolaldehyde. It can be seen that glucose degradation in presence of tungsten results in the formation of mannose, rather than formation of fructose (Example 5 and 6). Mannose is an epimer of glucose and can be converted in the hydrogenolysis reactor to MEG with the same efficiency as glucose (theoretical carbon selectivity of 100% to EG). Glucose conversion/degradation in presence of tungsten therefore results in a very high selectivity towards desired products. The selectively towards desired products is much higher than in absence of W (Example 5 and 6).

TABLE 5

| t (s) | T °C. | Glucose conversion % | yield fructose | mannose | Other* | Selectivity desired products % | Selectivity undesired products % |
|---|---|---|---|---|---|---|---|
| 5  | 195 | 4.0  | n.d. | 2.34  | 0.20  | 63.72 | 0.00 |
| 10 | 195 | 7.8  | n.d. | 3.85  | 0.00  | 49.24 | 0.00 |
| 15 | 195 | 12.0 | n.d. | 5.53  | 1.02  | 54.36 | 0.00 |
| 5  | 215 | 11.7 | n.d. | 5.79  | 1.23  | 59.74 | 0.00 |
| 10 | 215 | 27.1 | n.d. | 12.24 | 3.32  | 57.39 | 0.00 |
| 15 | 215 | 43.2 | n.d. | 19.50 | 5.94  | 58.88 | 0.00 |
| 5  | 230 | 32.3 | n.d. | 13.36 | 10.35 | 72.31 | 1.07 |
| 10 | 230 | 63.0 | n.d. | 23.10 | 21.32 | 69.00 | 1.48 |
| 15 | 230 | 78.7 | n.d. | 21.96 | 29.25 | 62.88 | 2.16 |

*other identified products
n.d. = not detected

Example 8 (Representative of the Invention)

A solution of 1 wt % of glucose+buffer (3 g/L acetic acid+6 g/L sodium acetate)+2500 ppm W (in the form of sodium metatungstate) (molar ratio Na:W=5.4) was fed to the reactor and the glucose conversion was studied at 5, 10 and 15 seconds residence time at temperatures of 195 to 215° C.

Results are tabulated in Table 6. As with Example 7, formation of fructose was not observed in these experiments. Mannose was a major component formed in these experiments. Other identified products include erythrose, threose, glyceraldehyde, MPG and glycolaldehyde.

Glucose conversion/degradation in presence of W and Na-containing buffer results in a very high selectivity towards desired products. This selectivity is higher than in presence of tungsten alone (>72.3%, Example 7), when the glucose conversion is below <25 wt %.

The selectively towards desired products is significantly higher (from 93.3 to 35.3%) over the whole range of glucose conversion, than in absence of tungsten (<23%, Example 5 and 6).

TABLE 6

| t (s) | T °C. | Glucose conversion % | yield fructose | mannose | Other* | Selectivity desired products % | Selectivity undesired products % |
|---|---|---|---|---|---|---|---|
| 5  | 195 | 5.8  | n.d. | 4.60  | 0.86  | 93.27 | 0.00 |
| 10 | 195 | 13.9 | n.d. | 8.03  | 3.84  | 81.84 | 3.37 |
| 15 | 195 | 21.3 | n.d. | 10.25 | 7.15  | 76.94 | 4.58 |
| 5  | 215 | 24.0 | n.d. | 12.33 | 8.25  | 81.53 | 4.35 |
| 10 | 215 | 47.9 | n.d. | 12.31 | 20.44 | 59.94 | 8.39 |
| 15 | 215 | 66.2 | n.d. | 11.34 | 27.50 | 49.95 | 8.73 |
| 5  | 230 | 54.0 | n.d. | 12.83 | 23.98 | 59.93 | 8.24 |
| 10 | 230 | 84.5 | n.d. | 8.27  | 37.70 | 44.05 | 10.36 |
| 15 | 230 | 94.9 | n.d. | 4.84  | 40.28 | 35.31 | 12.24 |

*other identified products
n.d. = not detected

In Examples 5 to 6, glucose conversion/degradation in absence or presence of buffer (and absence of tungsten) resulted in a very low selectivity to desirable products (<20%). A dominant product formed is fructose. Fructose will mainly form C3 components under the conditions in a hydrogenolysis reactor, rather than ethylene glycol. Therefore, partial conversion of glucose feedstock under these conditions will negatively affect the potential ethylene glycol yield that can be obtained in the hydrogenolysis reactor.

In Examples 7 and 8, glucose was still converted when in presence of tungsten (and buffer) but the conversion happens with a high selectivity towards desired products. For example, mannose is formed instead of fructose when tungsten is present. The mannose is an epimer of glucose and can still undergo the same chemistry in the hydrogenolysis reactor to yield MEG. The selectivity to desired products during the partial saccharide feedstock degradation is above 60%, while the glucose conversion stays below 50%. The presence of a buffer (increasing the molar ratio of Na:W) has a positive effect on the selectivity towards desired products as long as the glucose conversion stays below 50%.

It is postulated, without wishing to be bound by theory, that the presence of tungsten in the combined feed stream prevents conversion of glucose to fructose. The presence of mannose, instead of fructose, is advantageous as mannose will still undergo conversion to MEG in the reactor system. The molar ratio of alkali metal (sodium):tungsten stabilises the tungsten species present to enhance this effect and further increase the yield of MEG.

The invention claimed is:

1. A process for the preparation of glycols from a saccharide-containing feedstock in a reactor system, said process comprising:
   i) providing a first feed stream comprising said saccharide-containing feedstock in a first solvent at a temperature of no more than 160° C.;
   i) providing a second feed stream comprising a tungsten-based retro-aldol catalytic species and an alkali metal containing species in a second solvent at a temperature in the range of from 150 to 250° C.;
   iii) combining the first feed stream and the second feed stream, before they are provided to the reactor system, to form a combined feed stream;
   iv) providing the combined feed stream to the reactor system and operating the reactor at a temperature in the range of from 150° C. to 250° C.; and
   v) also contacting the combined feed stream with a hydrogenation catalytic species in the presence of hydrogen, wherein the molar ratio of alkali metal:tungsten in the combined feed stream is in the range of from 0.55 to 6.

2. The process as claimed in claim 1, wherein the alkali metal in the alkali metal containing species is sodium.

3. The process as claimed in claim 1, wherein the temperature of the first feed stream is maintained such that no more than 5 wt % of the saccharide contained therein undergoes any conversion, prior to the first feed stream being combined with the second feed stream.

4. The process as claimed in claim 1, wherein the combined feed stream is maintained at a temperature such that, when the combined feed stream is provided to the reactor system, in the range of from 0.5 to 50 wt % of the saccharide has undergone conversion.

5. The process as claimed in claim 1, wherein the molar ratio of alkali metal:tungsten in the combined feed stream is in the range of from 0.55 to 3.

6. The process as claimed in claim 1, wherein a product stream is removed from the reactor system and said product stream is separated into at least a glycol product stream and a hydrocarbon heavies stream.

7. The process as claimed in claim 6, wherein at least a portion of the hydrocarbon heavies stream is recycled to form at least a portion of the second feed stream.

8. The process as claimed in claim 1, wherein the pH in the reactor system is at least 2.0 and at most 8.0 and is maintained by using a buffer.

9. The process as claimed in claim 1, wherein the alkali metal containing species is present as or derived from the buffer and/or the tungsten-based retro-aldol catalytic species present in the reactor system.

10. The process as claimed in claim 1, wherein hydrogen is provided to the reactor system and not to the first feed stream, the second feed stream or the combined feed stream.

\* \* \* \* \*